(12) United States Patent
Ike

(10) Patent No.: US 7,181,049 B2
(45) Date of Patent: Feb. 20, 2007

(54) AUTHENTICATION OBJECT IMAGE-PICKUP METHOD AND DEVICE THEREFOR

(75) Inventor: Takahiro Ike, Yokohama (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 719 days.

(21) Appl. No.: 10/332,783

(22) PCT Filed: Apr. 26, 2002

(86) PCT No.: PCT/JP02/04269

§ 371 (c)(1),
(2), (4) Date: Jan. 10, 2003

(87) PCT Pub. No.: WO02/093482

PCT Pub. Date: Nov. 21, 2002

(65) Prior Publication Data

US 2003/0108224 A1 Jun. 12, 2003

(30) Foreign Application Priority Data

May 11, 2001 (JP) ............................ 2001-141710

(51) Int. Cl.
*G06K 9/00* (2006.01)
*H04N 5/232* (2006.01)
(52) U.S. Cl. ...................... 382/117; 348/354
(58) Field of Classification Search ................ 382/117; 348/354
See application file for complete search history.

(56) References Cited

U.S. PATENT DOCUMENTS 6,055,322 A * 4/2000 Salganicoff et al. ........ 382/117
6,091,452 A * 7/2000 Nishiyama .................. 348/349
6,215,891 B1 * 4/2001 Suzaki et al. ............... 382/117
6,704,054 B1 * 3/2004 Hashimoto .................. 348/354

FOREIGN PATENT DOCUMENTS

| JP | 6-205268 | 7/1994 |
|---|---|---|
| JP | 8-504979 | 5/1996 |
| JP | 2000-23946 | 1/2000 |
| JP | 2000-131598 | 5/2000 |
| JP | 2000-139878 | 5/2000 |
| JP | 2001-13401 | 1/2001 |

* cited by examiner

*Primary Examiner*—Joseph Mancuso
*Assistant Examiner*—Kathleen Yuan
(74) *Attorney, Agent, or Firm*—Pearne & Gordon LLP

(57) ABSTRACT

In an iris image pickup method in which an image signal picking up an iris is allowed to pass through a high-pass filter (41L) and a lens position in which an output of the high-pass filter (41L) indicates a peak value is searched by a mountaineering method, thereby capturing an iris image focused on the iris, when an amount of a high luminance component included in the image signal is equal to or greater than a predetermined value, a peak position of a high frequency component in the image signal passing through a narrow-band high-pass filter (41H) for causing only a high band in a pass band of the high-pass filter (41L) to pass therethrough is obtained by searching for a whole area within a predetermined range in place of a search for a focusing position by the mountaineering method, and is set to be an iris focusing position. Consequently, it is possible to acquire a clear iris image having a high authentication rate which is focused on the iris in place of glasses. Also in the case in which an authentication object person wears the glasses, consequently, an image focused on the iris can be acquired.

14 Claims, 8 Drawing Sheets

AUTHENTICATION OBJECT IMAGE-PICKUP METHOD AND DEVICE THEREFOR

TECHNICAL FIELD

The present invention relates to an authentication object image pickup method and apparatus to be used in a security system, and more particularly to an authentication object image pickup method and apparatus capable of acquiring an authentication object image focused on an authentication object also in the case in which the object wears glasses.

BACKGROUND ART

In a security system, for example, there has been known a method of carrying out an authentication by using the pattern of an individual iris as described in Japanese Patent Publication No. 8-504979 and Japanese Patent Publication No. 2000-23946. The authenticating method using an iris has an advantage that an image can be picked up by a camera in a distant place in no contact with an iris differently from a fingerprint, and has been therefore expected to spread in the future.

An iris image pickup apparatus to be used for an individual authentication employs an automatic focusing technique described in Japanese Patent Publication No. 2000-131598, for example, in order to acquire a clear iris image focused on an iris. The automatic focusing technique utilizes the fact that more high frequency components are included in an image pickup signal when an object is focused so that an outline image is clearly picked up, and searches for a lens position in which the high frequency component included in the picked up image signal has a peak while changing the lens position. In order to rapidly search for a peak position, there is generally employed a so-called mountaineering method for gradually changing the lens position in such a direction that the high frequency component is increased (the search is not carried out in such a direction that the high frequency component is decreased).

A high frequency component included in an image clearly picking up the outline of an iris has a high frequency. For example, therefore, it is possible to find an iris focusing position with high precision by carrying out the search through a high-pass filter H for causing the image pickup signal to pass through 1 MHz to 2 MHz. As shown in FIG. 8, however, a characteristic line VH of a high frequency component passing through the high-pass filter H is almost flat in portions other than a peak point A. In the case in which the peak position is to be searched by employing the mountaineering method, therefore, there is a high possibility that a computer cannot decide whether the search is to be carried out in a rightward direction (the lens position is set in an FAR direction) or a leftward direction (the direction of the lens is set in an NEAR direction), and furthermore, a peak position B caused by a noise might be erroneously detected as a focusing position.

For this reason, if the search is carried out by using, as the high-pass filter, a high-pass filter L for passing through 300 kHz to 2 MHz including a lower frequency band, for example, in place of the high-pass filter H having a narrow band described above, a characteristic line VL is greatly changed vertically as shown in FIG. 8. Consequently, it is possible to easily search for a peak position C by the mountaineering method. Thus, the search can rapidly be carried out. For this reason, in the case in which a focusing position is to be searched by the mountaineering method, the high-pass filter having a great band width is generally used.

In an iris authenticating apparatus to be used for a security system, it is possible to enhance an identification rate corresponding to a clearer iris image which is acquired. On the other hand, an authentication object person to be an object cannot be stationary for a long time. Therefore, it is necessary to focus a lens on the position of an iris in a short time. For this reason, the mountaineering method is usually used for the search in an iris image pickup apparatus to be used for the iris authenticating apparatus.

However, there is a problem if the authentication object person wears glasses. In the case in which the authentication object person wears the glasses, a high frequency component generated from the outline of an iris is hidden because the amount of a high frequency component generated by the frame or illumination reflection of the glasses is larger. Consequently, the image of the iris picked up in the lens position focused on the glasses is blurred or focusing cannot be carried out due to the illumination reflection of the glasses so that the identification rate is reduced.

DISCLOSURE OF THE INVENTION

The invention has been made in consideration of the circumstances and has an object to provide an authentication object image pickup method and apparatus capable of rapidly acquiring an image focused on an authentication object also in the case where an authentication object person wears glasses.

In order to achieve the object, the present invention provides an authentication object image pickup method and apparatus wherein when an image signal picking up an authentication object is caused to pass through a filter and a lens position in which an output of the filter indicates a peak value is searched by a mountaineering method, thereby capturing an image focused on the authentication object and an amount of a high luminance component included in the image signal is equal to or greater than a predetermined value, a peak position of a high frequency component in the image signal is obtained by searching for a whole area of a predetermined range in place of a search for a focusing position by the mountaineering method, and is set to be an authentication object focusing position. With such a structure, also in the case in which a large number of high luminance components are included in the image of the authentication object, the focusing position of the authentication object can be obtained in a short time.

It is preferable that the filter should be a narrow-band high-pass filter for causing only a high band of a frequency component in the image signal to pass therethrough. By using the narrow-band filter, it is possible to obtain a focusing position with high precision. Correspondingly, an authentication rate can be enhanced.

Moreover, it is preferable that the predetermined range should be determined by a distance to the authentication object which is measured by range means and that the predetermined range should be set to be a range of the measured distance±20% around the measured distance. If the predetermined range is small, a probability that the peak position will enter the same range is reduced. If the predetermined range is increased, a probability that the peak position will enter the same range is increased proportionally. On the other hand, if the predetermined range is increased, a processing of searching for the peak position takes a longer time. By setting the predetermined range to the range described above, it is possible to practically search for the peak position in a short time.

Furthermore, it is preferable that when the amount of the high luminance component included in the image signal is equal to or greater than the predetermined value, an illuminating direction for the authentication object should be switched to capture an image signal. By thus switching the illuminating direction, it is possible to acquire a suitable image for the authentication in which the amount of the high luminance component is less than the predetermined value.

Moreover, it is preferable that when the amount of the high luminance component is not smaller than the predetermined value even if the illuminating direction for the authentication object is switched, the authentication object should be illuminated in such an illuminating direction that the high luminance component is the smallest, thereby carrying out a processing of searching for the authentication object focusing position. By such a structure, it is possible to avoid such a situation that the image of the authentication object cannot be acquired, and furthermore, to easily search for the peak position.

Figure 1:
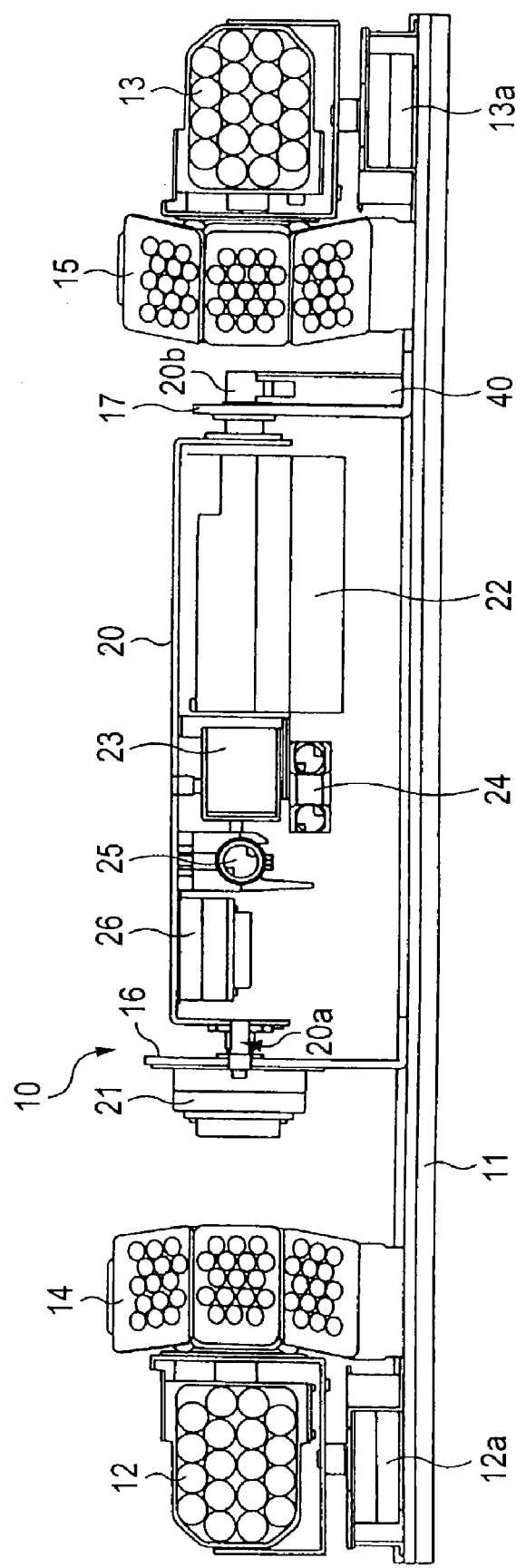
FIG. 1 is a front view showing a state in which the outer panel of an iris image pickup apparatus according to an embodiment of the invention is removed.

In the drawings, the reference numeral 10 denotes an iris image pickup apparatus, the reference numeral 12 denotes a left iris illuminator, the reference numeral 12*a* denotes a pan motor for a left iris illuminator, the reference numeral 12*b* denotes a tilt motor for a left iris illuminator, the reference numeral 13 denotes a right iris illuminator, the reference numeral 13*a* denotes a pan motor for a right iris illuminator, the reference numeral 13*b* denotes a tilt motor for a right iris illuminator, the reference numeral 21 denotes a tilt motor, the reference numeral 22 denotes a telephoto camera, the reference numeral 23 denotes a pan mirror, the reference numeral 24 denotes a range sensor, the reference numeral 25 denotes a wide angle camera, the reference numeral 26 denotes a pan motor, the reference numeral 41 denotes a high-pass filter, the reference numeral 41*a* denotes a switch, the reference numeral 41L denotes a wide-band high-pass filter, the reference numeral 41H denotes a narrow-band high-pass filter, and the reference numeral 60 denotes a high luminance determination section.

BEST MODE OF CARRYING OUT THE INVENTION

An embodiment of the invention will be described below with reference to the drawings.

Figure 2:
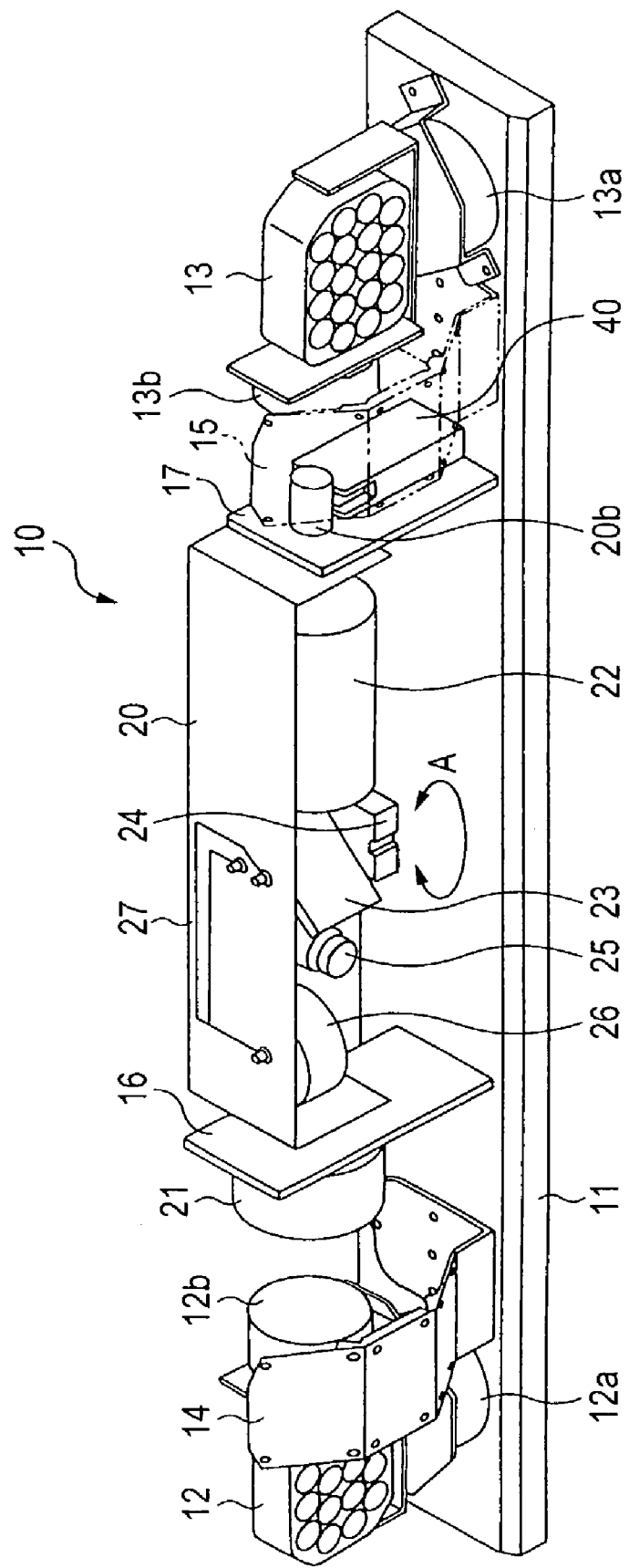
FIG. 2 is a perspective view showing the iris image pickup apparatus according to the embodiment of the invention.

FIG. 1 is a front view showing an iris image pickup apparatus according to an embodiment of the invention, and FIG. 2 is a perspective view showing the same apparatus. In both drawings, a panel to be provided on the outside is not shown.

An iris image pickup apparatus 10 according to the embodiment has an longitudinal fixing table 11. Iris illuminators 12 and 13 are attached to the left and right ends of the fixing table 11, respectively. A condensing lens for collecting an infrared light to an iris and for carrying out illumination is attached to each of the iris illuminators 12 and 13, and the iris illuminators 12 and 13 are provided with pan motors 12*a* and 13*a* for illumination and tilt motors 12*b* and 13*b* for illumination such that an illumination light is turned in the direction of an iris.

Illuminators 14 and 15 for a wide angle camera are attached to the inner side (the central side of the fixing table 11) of the iris illuminators 12 and 13, respectively. The illuminators 14 and 15 are constituted as a set of a large number of light emitting diodes, and each light emitting diode is not shown and only an attachment plate for attaching the light emitting diode is shown in the perspective view of FIG. 2. Since it is sufficient that the illuminators 14 and 15 can be uniformly illuminated in a wide range by an infrared light (because the operations of a pan and a tilt are not required), they are fixed to the fixing table 11 and the condensing lens is not provided.

A support plate 16 is erected on the fixing table 11 at the inner side of the illuminator 14 (the central side of the fixing table 11), and a support plate 17 is erected on the fixing table 11 at the inner side of the illuminator 15 (the central side of the fixing table 11). A tilt table 20 is attached between both of the support plates 16 and 17.

The tilt table 20 is provided with axes 20*a* and 20*b* on the left and right, and the axes 20*a* and 20*b* are rotatably supported on the support plates 16 and 17, respectively. The axis 20*a* is directly coupled to the rotating shaft of a tilt motor 21 which is attached to the support plate 16, and a damper 40 is attached to the axis 20*b*.

A telephoto camera (a narrow angle camera) 22, a pan mirror 23, a range finder (a range sensor) 24, a wide angle camera 25 and a pan motor 26 are mounted on the tilt table 20. The telephoto camera 22 is provided on the support plate 17 side of the tilt table 20 in such a manner that an optical axis thereof is coaxial with the rotating shaft of the tilt table 20. The pan mirror 23 is provided in the position of the front surface of the telephoto camera 22, and a light reflected by the pan mirror 23 is incident on the telephoto camera 22. The pan mirror 23 is vertically rotatable around the optical axis of the telephoto camera 22, that is, in a direction of a double-headed arrow A in FIG. 2.

The pan motor 26 to drive the pan mirror 23 in the direction of the arrow A is attached to the support plate 16 side of the tilt table 20 and serves to drive the pan mirror 23 through a link mechanism 27. The range finder 24 is driven in the direction of the arrow A interlockingly with the pan mirror 23, and can always measure a distance with high precision by irradiating the infrared light on an object from just the front. The range finder 24 is also driven by the pan motor 26 through the link mechanism 27.

The wide angle camera 25 is provided between the pan mirror 23 and the pan motor 26 and has an optical axis provided in a position crossing the rotating shaft of the tilt table 20. Consequently, a parallax in a vertical direction between the wide angle camera 25 and the telephoto camera 22 is eliminated.

Figure 3:
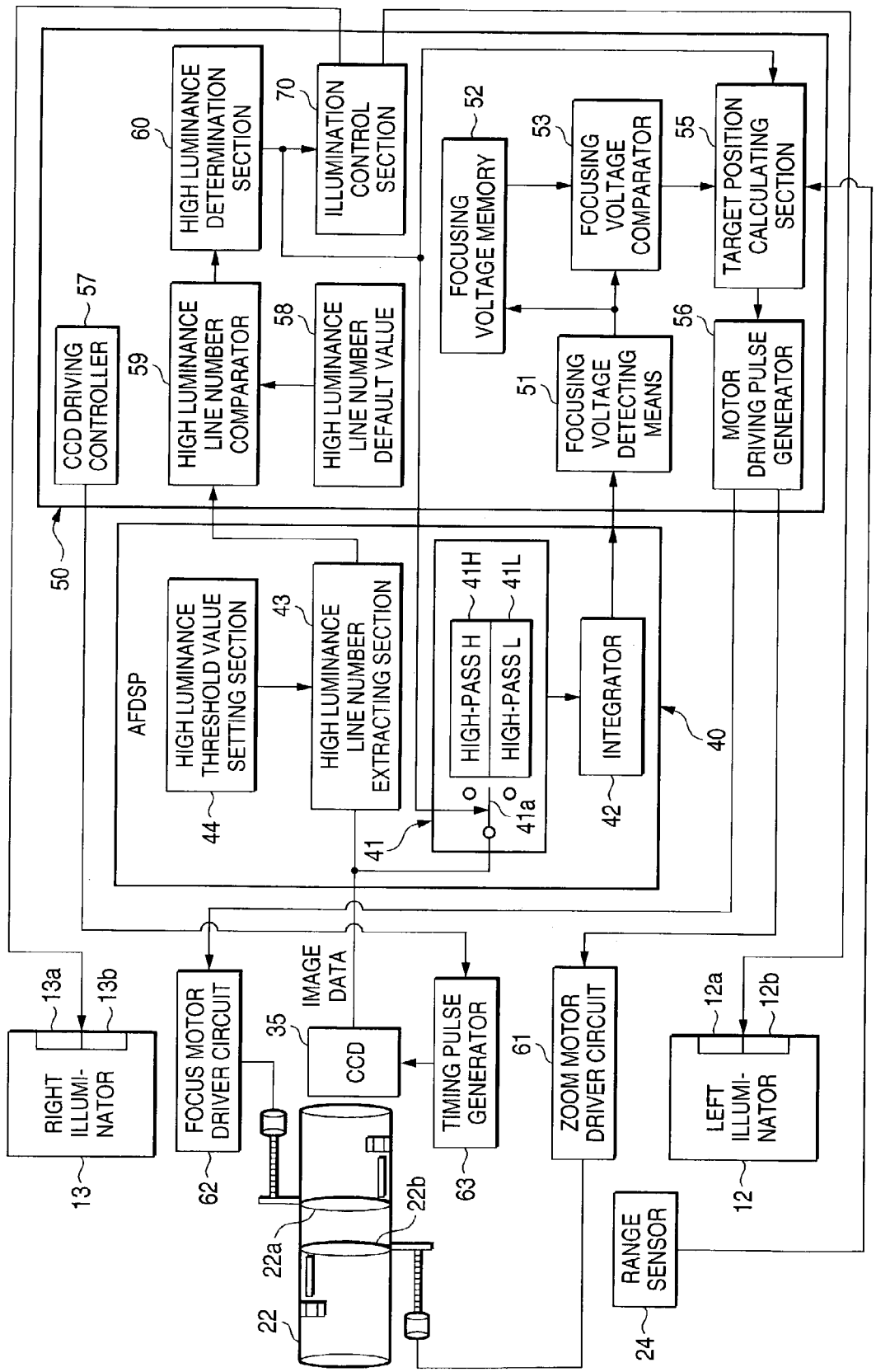
FIG. 3 is a diagram showing the structure of a controller to be mounted on the iris image pickup apparatus according to the embodiment of the invention.

FIG. 3 is a functional block diagram showing a controller for controlling the iris image pickup apparatus having the structure described above. The controller includes image pickup means provided in the telephoto camera 22, for example, an AFDSP (Auto Focus Digital Signal Processor) 40 for capturing an image signal from a CCD 35 and outputting the integral value of a high frequency component in the image signal, control means 50, a zoom motor driver circuit 61 and a focus motor driver circuit 62 which serve to output a motor driving current in response to an instruction output sent from the control means 50, and a timing pulse generator 63 for outputting a timing pulse to the CCD 35 based on the instruction output sent from the control means 50.

The CCD 35 includes image pickup elements having approximately 300 thousand pixels in total of 640 vertical lines by 480 horizontal lines in a matrix, and image pickup data of all the pixels of 480 lines in wide are output to the AFDSP 40 or thinned data of pixels in 96 lines every predetermined lines, for example, every five lines in a lateral line (or a vertical line) are output to the AFDSP 40 in response to an instruction sent from the timing pulse generator 63.

The AFDSP 40 includes a high-pass filter 41 for extracting only a high frequency signal having a high frequency band from the image signal captured from the CCD 35, an integrator 42 for integrating a high frequency band passing through the high-pass filter 41 with an AF zone set to be a zone for focusing in an image, a high luminance line number extracting section 43 for extracting the number of a high luminance line in the AF zone, and a high luminance threshold value setting section 44 for giving a threshold value to the high luminance line number extracting section 43. When the output of the integrator 42, that is, the amount of a high frequency component is increased, a screen becomes sharper and an image is more focused. Therefore, a voltage corresponding to the output of the integrator 42 is referred to as a focusing voltage.

The high-pass filter 41 of the AFDSP 40 mounted on the iris image pickup apparatus 10 according to the embodiment includes a high-pass filter (H) 41H and a high-pass filter (L) 41L, and a switch 41a for selecting one of the high-pass filters in response to the output signal of a high luminance determination section 60 which will be described below. The high-pass filter (H) 41H allows a high frequency component between 1 MHz to 2 MHz in the image signal extracted from the CCD 35 to pass through the integrator 42, and the high-pass filter (L) 41L allows a high frequency component between 300 kHz to 2 MHz in the image signal extracted from the CCD 35 to pass through the integrator 42.

The control means 50 includes focusing voltage detecting means 51 for detecting the output of the integrator 42, a focusing voltage memory 52 for retaining a focusing voltage value obtained before moving a lens, a focusing voltage comparator 53 for comparing the detection value of the focusing voltage detecting means 51 with the contents of the focusing voltage memory 52, a target position calculating section 55 for calculating the movement target position of a lens in response to the output of the comparator 53 and the output of the range sensor 24, and a motor driving pulse generator 56 for generating a pulse to move each lens by a difference between a movement target position of each of a focus lens 22a and a zoom lens 22b output from the target position calculating section 55 and a current position and for outputting the pulse to each of the driver circuits 61 and 62.

The target position calculating section 55 carries out a processing of moving a lens in such a direction as to increase a focusing voltage by setting the measuring position of the range sensor 24 as a starting point when the switch 41a selects the high-pass filter 41L in response to a determination signal sent from the high luminance determination section 60 which will be described below (a focusing position search processing using a mountaineering method), and a processing of searching for a predetermined range around the measuring position of the range sensor 24 to obtain the peak position of a focusing voltage, thereby moving a lens position to the peak position when the switch 41a selects the high-pass filter 41H (a focusing position search processing within a predetermined range with glasses worn by an object).

The control means 50 further includes a high luminance line number default value setting section 58, a high luminance line number comparator 59 for comparing a high luminance line number in a thinned image which is extracted by the high luminance line number extracting section 43 with a default value thereof (the output value of the setting section 58), the high luminance determination section 60 for determine whether or not the high luminance line number thus detected is greater than the default value, and an illumination controller 70 for controlling the pan motors 12a and 13a and the tilt motors 12b and 13b in the left and right illuminators 12 and 13 or for controlling the number of diodes to be turned on by the illuminators 12 and 13 when the high luminance determination section 60 determines a high luminance line number (K)≧ default value (D).

Figure 4:
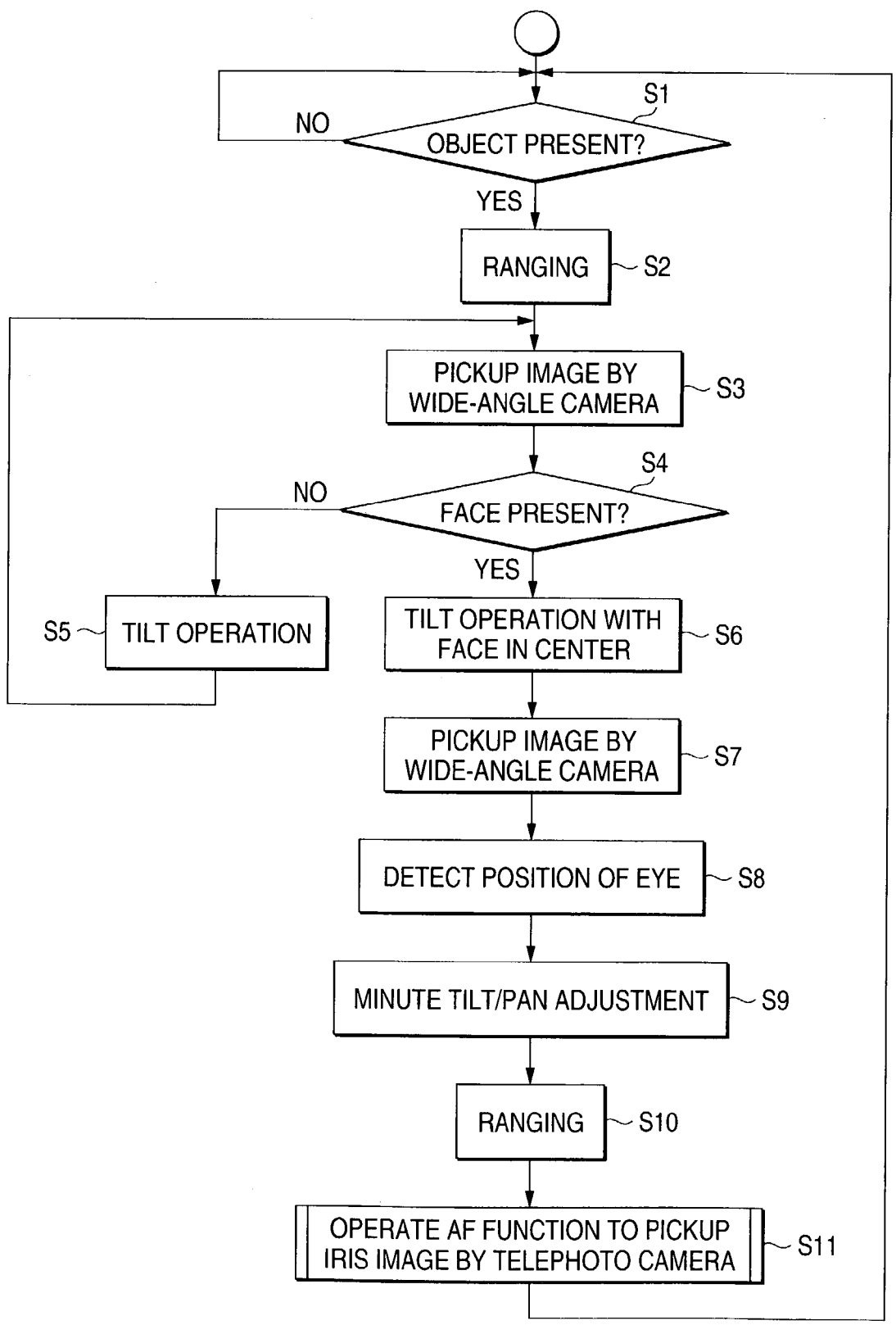
FIG. 4 is a flow chart showing a procedure for the processing of the controller to be mounted on the iris image pickup apparatus according to the embodiment of the invention.

Next, description will be given to the operation of the iris image pickup apparatus having the above structure. FIG. 4 is a flow chart showing a procedure for the operation of the controller provided in the iris image pickup apparatus. First of all, an object (an authentication object person) entering a predetermined range of the front of the iris image pickup apparatus is waited. In the standby state, each of the motors 21, 26, 12a, 13a, 12b and 13b is placed in a default position (a home position) and the range finder 24 is also turned in just the front position as a default position.

Figure 5:
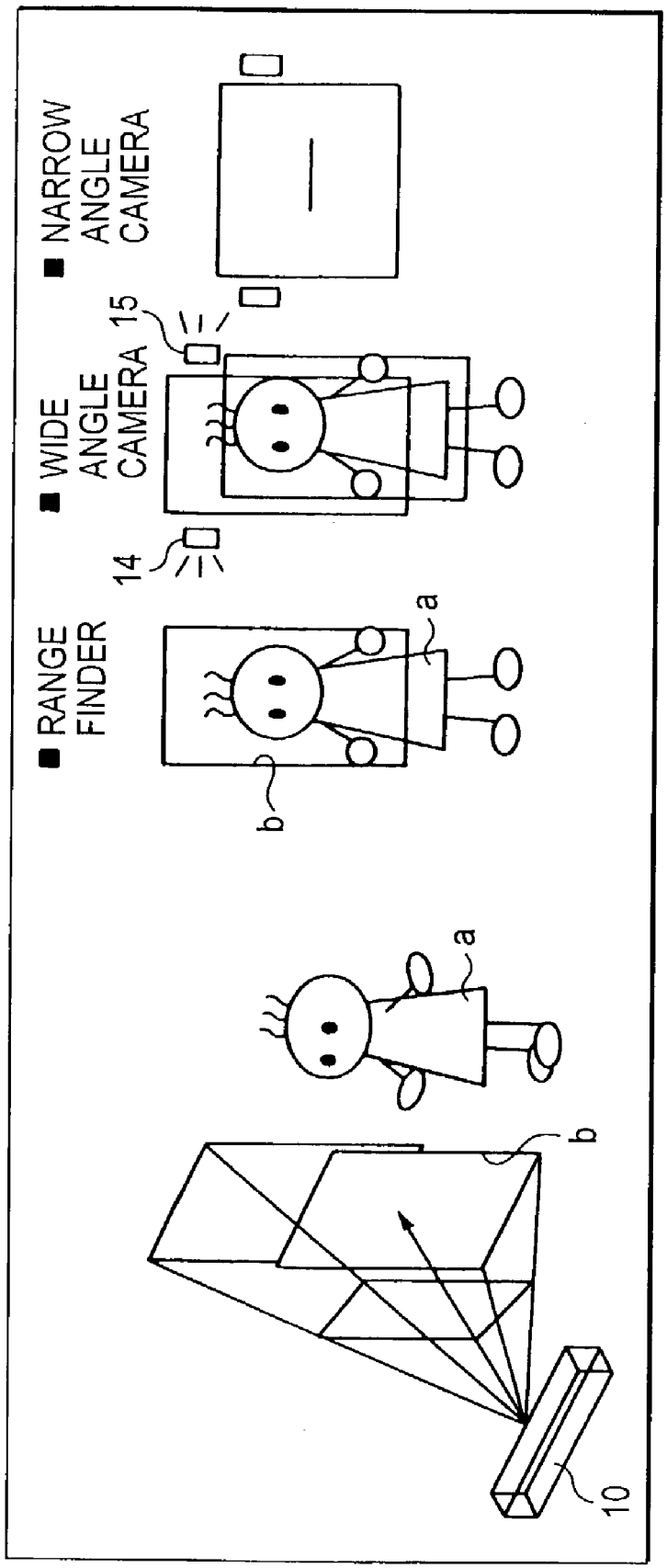
FIG. 5 is a view showing the image pickup state of a wide angle camera to be mounted on the iris image pickup apparatus according to the embodiment of the invention.

The range finder 24 emits an infrared light all the time or every predetermined time during the standby, and decides the presence of the object depending on the presence of a reflected light. For example, in the case in which an object a enters an image pickup range b of the iris image pick up apparatus 10 as shown in FIG. 5, a distance from the reflected light to the object a is measured (a step S2) and the wide angle camera 25 is focused based on the distance thus measured, and the processing proceeds to a next step S3. In the case in which the iris image pickup apparatus is applied to an ATM terminal in a bank, it is also possible to replace the standby processing of the object in the step S1 with the standby processing of starting the ATM operation of a person.

At the step S3, an image is picked up by the wide angle camera 25. At this time, the illuminators 14 and 15 for the wide angle camera are turned on. At a next step S4, whether a face is present in the pickup image is decided by a pattern matching processing. If the face is not present, a driving instruction is output to the tilt motor 21 to carry out a tilt operation (a step S5) and the image picked up by the wide angle camera is captured again at the step S3. The steps S3, S4 and S5 are repeated until the whole image of the face can be captured.

If a face pattern is present in the image picked up by the wide angle sensor, the processing proceeds from the step S4 to a step S6 in which the tilt operation of the tilt table 20 is carried out such that the face is set onto the center of the image pickup screen of the wide angle camera and the pan and tilt positions of the iris illuminators 12 and 13 in FIG. 1 are also adjusted to previously turn the direction of the irradiation of an illumination light such that the illumination light is irradiated on the face. Furthermore, the pan mirror 25 is also turned previously in such a manner that the telephoto camera 22 can pickup the image of the face. The minute adjustment is carried out at a step S9 as will be described below. Then, an image is picked up again by the wide angle camera at a next step S7 and the processing proceeds to a step S8.

At the next step S8, the position of at least one of left and right eyes is detected from the image picked up by the wide angle camera which is captured at the step S7. Subsequently, the position of the eye obtained at the step S8 is converted to the coordinates of the telephoto camera 22 to obtain the precise tilt position of the tilt table 20 and the precise pan position of the pan mirror 25, and the tilt and pan positions of the illuminators 12 and 13, thereby adjusting the tilt position and the pan position in such a manner that the telephoto camera 22 catches an iris with high precision, and at the same time, the focused illumination light of each of the iris illuminators 12 and 13 is irradiated on the iris (a step S9).

At a next step S10, a distance to the iris is measured by the range finder 24. The range finder 24 adjusts the direction of the measurement interlockingly with the adjustment of the pan position of the pan mirror 23. Therefore, an infrared light for measurement is irradiated toward the iris and the light reflected by cheeks below eyes is received, for example, so that the distance to the iris can be measured with high precision.

At a next step S11, the distance to the iris which is measured at the step S10 is preset to the telephoto camera 22 and the focus lens 22a (FIG. 3) is rapidly driven to be focused on the distance, and the focusing position of the iris is subsequently searched as will be described below.

Figure 6:
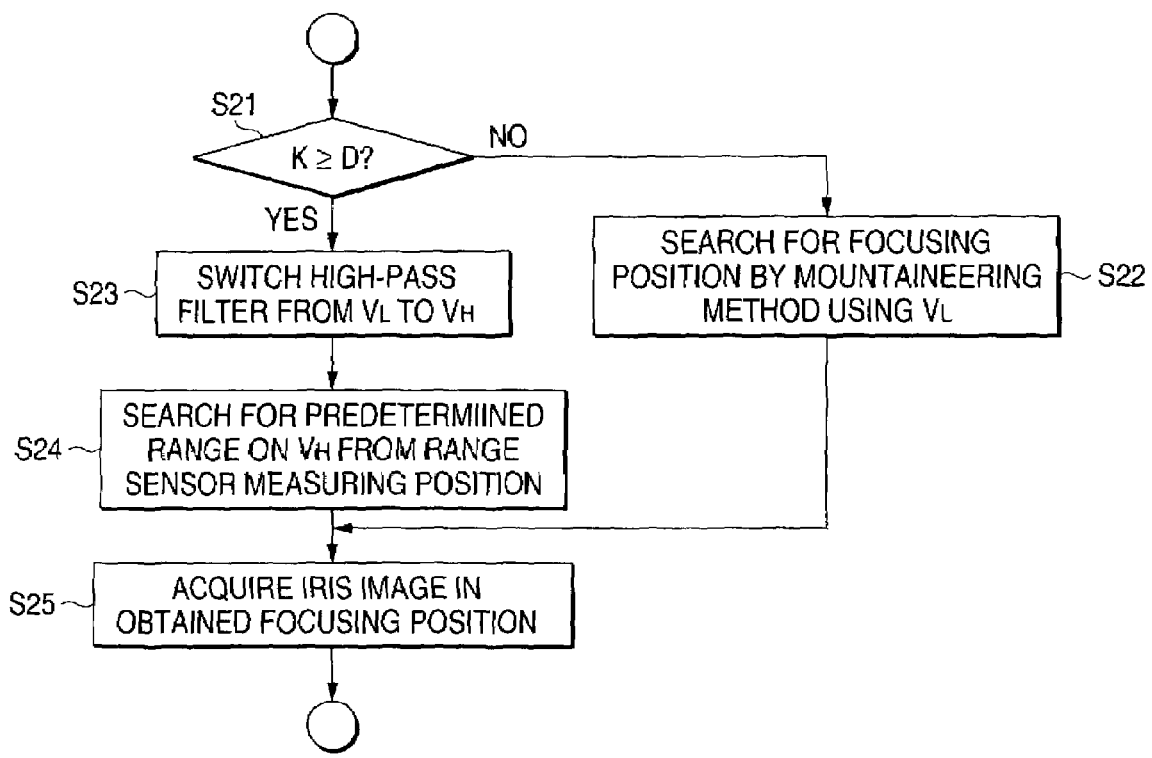
FIG. 6 is a flow chart showing the detailed procedure of a step S11 illustrated in FIG. 4.

FIG. 6 is a flow chart showing the detailed processing procedure of the step S11. When the processing proceeds to the step S11, it is first determined whether or not a high luminance line number K at which a luminance exceeds a threshold value is equal to or greater than a set value D at a step S21. In the case in which an object wears glasses and is in a position in which the illumination light of an iris overlaps with the iris, the high luminance line number in an AF zone is increased. The result of the determination in the step S21 is YES. If the object does not wear the glasses, the result of the determination in the step S21 is NO.

In the case in which the result of the determination in the step S21 is NO, a determination signal indicative of no high luminance is output from the high luminance determination section 60 in FIG. 3 to the switch 41a and the wide-band high-pass filter 41L is selected. At a next step S22, the peak position of a focusing voltage is searched in a direction of an arrow X by setting the measuring position of the range sensor (range finder) 24 to be a starting point by the mountaineering method using a characteristic line VL shown in FIG. 7. For the search of the peak position, the motor for focus lens driving is moved every step to acquire an iris image by the telephoto camera 22, thereby setting, as a peak position, a focus lens position in which the amount of a high frequency component in the image is the largest. The peak position thus searched is a focusing position for the iris because the object does not wear the glasses.

In the case in which the result of the determination in the step S21 is YES (it is determined that the object wear the glasses), a determination signal indicative of a high luminance is output from the high luminance determination section 60 to the switch 41a in FIG. 3 so that switching to the narrow-band high-pass filter 41H is carried out (a step S23). Then, the processing proceeds to a next step S24 in which a predetermined range Y provided around the measuring position of the range sensor 24, for example, a range of a range sensor measured value ±20% is wholly searched and a peak position within the same range is obtained. This search is also carried out by moving the motor for focus lens driving every step in the same manner as described above.

Figure 7:
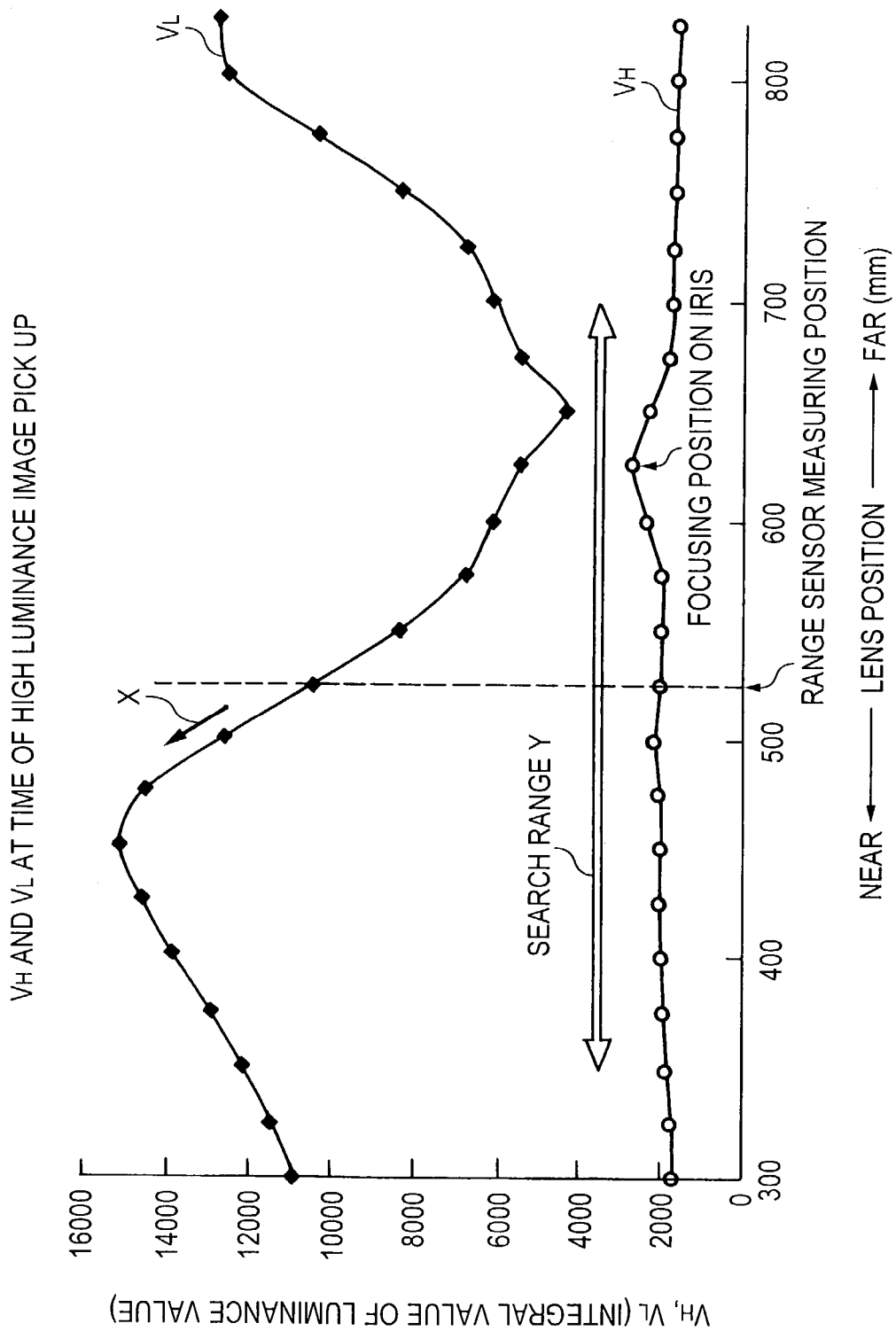
FIG. 7 is a chart showing the search range of the iris image pickup apparatus according to the embodiment of the invention.
Figure 8:
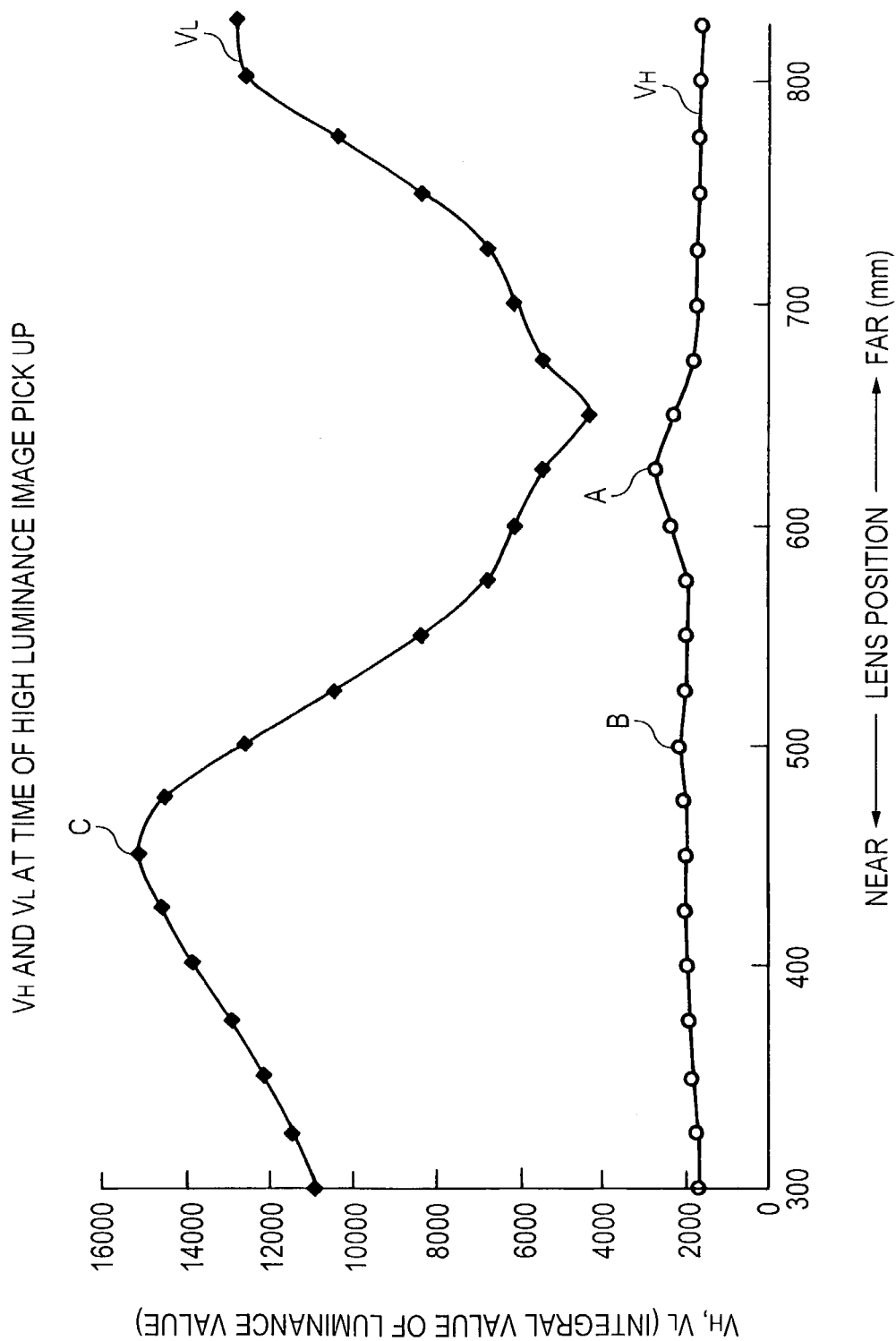
FIG. 8 is a high frequency component characteristic chart showing a wide-band high-pass filter output (VL) and a narrow-band high-pass filter output (VH).

As shown in FIG. 7, a frequency characteristic line VH of a signal passing through the narrow-band high-pass filter 41H is flat in portions other than a peak point, and the peak point is placed in a position focused on the iris. In the case in which the object wears the glasses, accordingly, it is possible to find the focusing position of the iris with high precision in a short time by searching for the focusing position within a predetermined range on the VH.

If the predetermined range Y is small, a probability that the peak position will enter the range is reduced. If the predetermined range is increased, the probability that the peak position will enter the range is increased. On the other hand, when the predetermined range Y is increased, a longer time is taken for the processing of searching for the peak position. By setting the predetermined range to be the range of the range sensor measured value ±20%, it is possible to practically search for the peak position in a short time. If the performance of the iris image pickup apparatus 10 is enhanced so that the movement of the focus lens every step is carried out more quickly, and furthermore, a CPU performance for carrying out a pickup image capturing processing or a search processing is increased, it is also possible to change the value of ±20% to ±25% or ±30%. After the focusing position of the iris is obtained at the steps S22 and S24, the processing proceeds to a next step S25 in which an iris image picked up in the focusing position is set to be an authentication object image and the processing in FIG. 4 is ended to transfer the iris image to the authenticating apparatus side which is not shown.

In the embodiment, thus, the method of searching for the iris focusing position is changed depending on whether an authentication object person wears the glasses (whether the high luminance line number in the pickup image is greater than the set value). Therefore, it is possible to obtain the iris focusing position with high precision in a short time.

Although the method of searching for the iris focusing position is changed while switching the two high-pass filters having wide and narrow bands in the embodiment, the bands of the two high-pass filters overlap on the high-band side and they may be therefore used in parallel to search for a peak within a predetermined range using the characteristic line VH if it is decided that the object wears the glasses (K≧D).

At the step S22, moreover, it is also possible to further obtain a peak position by the mountaineering method on the VH after acquiring the peak position by the mountaineering method on the VL in FIG. 7, in order to enhance the precision in the search. In the case in which the object does not wear the glasses, the peak position obtained from the characteristic line VL does not approach the flat portion of the characteristic line VH but the crest of a peak (both of the peak positions are not greatly shifted from each other). Therefore, the mountaineering method using the characteristic line VH can be applied, and furthermore, the peak position on the VH is coincident with the iris focusing position with higher precision than the peak position on the VL.

The relationship with the iris illuminating direction has not been described in detail. If it is possible to change the direction of the illumination of the iris (to carry out switching to the illumination of only the iris illuminator 13 on the left side or to change the direction of the irradiation of the iris illuminator by the tilt and pan motors when K≧D is obtained by the illumination of only the iris illuminator 12 on the right side), thereby capturing an image in which an iris illumination light is not reflected by glasses if an object wears the glasses, the processing proceeds to the step S22 in FIG. 6 in which it is possible to search for the iris focusing position with high precision by the mountaineering method. When the high luminance line number cannot be set to be smaller than the set value D even if the direction of the illumination of the iris is switched, the iris is illuminated in the direction of the illumination of the iris in which the high luminance line number is the smallest so that the focusing position can also be obtained in the step S23. The reason is that the peak position can be searched with higher precision if the high luminance line number is decreased.

While the description has been given by setting the iris to be the authentication object in the embodiment, it is also possible to use a retina in place of the iris. Moreover, it is also possible to pattern the feature of a face, thereby setting the pattern of the face to be the authentication object.

While the invention has been described in detail with reference to the specific embodiment, it is apparent to the skilled in the art that various changes and modifications can be made without departing from the spirit and scope of the invention.

The application is based on Japanese Patent Application (Japanese Patent Application No. 2001-141710) filed on May 11, 2001 and the contents thereof are incorporated herein by reference.

INDUSTRIAL APPLICABILITY

According to the invention, it is possible to acquire an image focused on an authentication object in a short time also in the case in which an authentication object person wears glasses, and furthermore, it is possible to enhance the authentication rate of the authentication object.

The invention claimed is:

1. An authentication object image pickup method comprising:
   allowing an image signal obtained by picking up an authentication object to pass through a filter;
   searching a lens position in which an output of the filter indicates a peak value by a mountaineering method;
   searching a peak position of a high frequency component in the image signal obtained by searching for a whole area within a predetermined range;
   capturing an image focused on the authentication object;
   determining whether an amount of a high luminance component included in the image signal is equal to or greater than a predetermined value;
   switching between the searching process of the peak position of the high frequency component and the searching process by the mountaineering method based on a result of the determining process; and
   setting the peak position or a focusing position corresponding to the lens position to an authentication object focusing position.

2. The authentication object image pickup method according to claim 1, wherein the filter is a narrow-band high-pass filter for allowing only a high band of a frequency component in the image signal to pass therethrough.

3. The authentication object image pickup method according to claim 1, wherein the predetermined range is determined by a distance to the authentication object measured by ranging means.

4. The authentication object image pickup method according to claim 3, wherein the predetermined range is set to be a range of the measured distance ±20% around the measured distance.

5. The authentication object image pickup method according to any of claims 1 to 4, wherein when the amount of the high luminance component included in the image signal is equal to or greater than the predetermined value, an illuminating direction for the authentication object is switched to capture the image signal.

6. The authentication object image pickup method according to claim 5, wherein when the amount of the high luminance component is not smaller than the predetermined value even if the illuminating direction for the authentication object is switched, the authentication object is illuminated in such an illuminating direction that the high luminance component is the smallest, thereby carrying out a processing of searching for the authentication object focusing position.

7. An authentication object image pickup apparatus comprising:
   image pickup means for picking up an image of an authentication object;
   a filter for allowing an image signal captured by the image pickup means to pass therethrough;
   control means for allowing the image pickup means to capture an image focused on the authentication object;
   means for searching for a lens position in which an output of the filter indicates a peak value by a mountaineering method;
   means for searching for a whole area within a predetermined range to obtain a peak position of a high frequency component in the image signal;
   determining means for determining whether an amount of a high luminance component included in the image signal is equal to or greater than a predetermined value;
   switching means for switching between the searching process of the peak position of the high frequency component and the searching process by the mountaineering method based on a result of the determining process; and
   setting means for setting the peak position or a focusing position corresponding to the lens position to an authentication object focusing position.

8. The authentication object image pickup apparatus according to claim 7, wherein the filter is a narrow-band high-pass filter for allowing only a high band of a frequency component in the image signal to pass therethrough.

9. The authentication object image pickup apparatus according to claim 7, wherein the predetermined range is determined by a distance to the authentication object measured by ranging means.

10. The authentication object image pickup apparatus according to claim 9, wherein the predetermined range is set to be a range of the measured distance ±20% around the measured distance.

11. The authentication object image pickup apparatus according to any of claims 7 to 10, wherein when the amount of the high luminance component included in the image signal is equal to or greater than the predetermined value, an illuminating direction for the authentication object is switched to capture the image signal.

12. The authentication object image pickup apparatus according to claim 11, wherein when the amount of the high luminance component is not smaller than the predetermined value even if the illuminating direction for the authentication object is switched, the authentication object is illuminated in such an illuminating direction that the high luminance component is the smallest, thereby carrying out a processing of searching for the authentication object focusing position.

13. The authentication object image pickup method according to claim 1, further comprising the step of performing the searching process of the peak position of the high frequency component when the amount of the high luminance component included in the image signal is equal to or greater than the predetermined value.

14. The authentication object image pickup apparatus according to claim 7, wherein when the amount of the high luminance component included in the image signal is equal to or greater than the predetermined value, the switching means switches to perform the searching process of the peak position of the high frequency component.

* * * * *